United States Patent [19]

Scotese et al.

[11] Patent Number: 4,537,968

[45] Date of Patent: Aug. 27, 1985

[54] THIOPHENE DERIVATIVES WITH ANTISECRETORY ACTIVITY

[75] Inventors: Anthony C. Scotese, King of Prussia; Robert L. Morris, Devon; Arthur A. Santilli, Havertown; Donald P. Strike, St. Davids, all of Pa.

[73] Assignee: American Home Products Corporation, New York, N.Y.

[21] Appl. No.: 564,440

[22] Filed: Dec. 21, 1983

[51] Int. Cl.³ .................. C07D 413/12; C07D 333/36; C07D 417/12

[52] U.S. Cl. ..................................... 546/209; 544/60; 544/146; 549/30; 549/70

[58] Field of Search ................... 546/209; 549/72, 30; 544/60, 146

[56] References Cited

FOREIGN PATENT DOCUMENTS 917854 2/1963 United Kingdom ................. 549/71

Primary Examiner—Robert T. Bond
Attorney, Agent, or Firm—George Tarnowski

[57] ABSTRACT

Compounds of the formula:

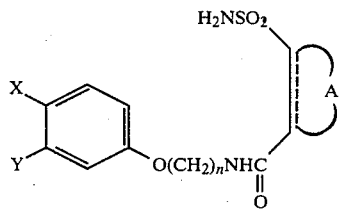

wherein

A is

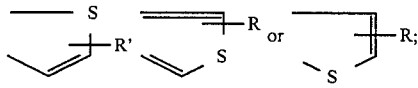

R is mono- or dihalo, amino, nitro, cyano, hydroxy, trifluoromethyl, mercapto, lower alkyl, lower alkoxy, alkanoyl, lower cycloalkyl, carboxy, alkoxycarbonyl, mono- or di-lower alkyl substituted amino, alkanoylamino, lower alkyl thio, loweralkyl-sulfonyl, sulfamoyl, lower alkyl substituted sulfamoyl, phenyl or phenyl substituted with halo, lower alkyl, lower alkoxy, trifluoromethyl, hydroxy, amino, cyano or nitro;

X and Y are each, independently, hydrogen or

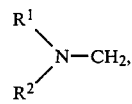

wherein $R^1$ is hydrogen or lower alkyl;

$R^2$ is hydrogen or lower alkyl; or $R^1$ and $R^2$ taken together form a heterocyclic moiety selected from 1-pyrrolidinyl, 1-piperidinyl, 1-hexahydroazepinyl, 1-octahydroazocinyl, 3-thiazolidinyl, 4-morpholinyl or 4-thiomorpholinyl, with the proviso that one of X and Y is always hydrogen;

n is 1–4;

and the pharmacologically acceptable salts thereof, which are intermediates in preparing $H_2$ receptor antagonists and which also have antisecretory/antiulcer activity.

2 Claims, No Drawings

THIOPHENE DERIVATIVES WITH ANTISECRETORY ACTIVITY

This invention relates to new thiophene-containing compounds having antisecretory/anti-ulcer activity.

In U.S. Ser. No. 468,221, now U.S. Pat. No. 4,490,527, there are disclosed compounds having the general formula:

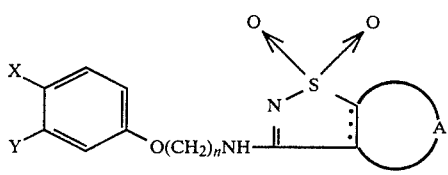

ps wherein A is any of

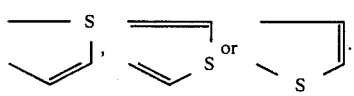

These compounds are disclosed to have activity as $H_2$-receptor antagonists as well as being antisecretory agents. It has now been found that the compounds of the present invention, which are intermediates in the preparation of the compounds disclosed in U.S. Ser. No. 468,221, now U.S. Pat. No. 4,490,527, are also themselves potent antisecretory/anti-ulcer agents.

The compounds of the invention have the formula:

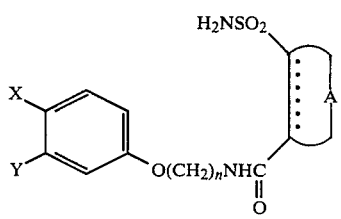

wherein A is

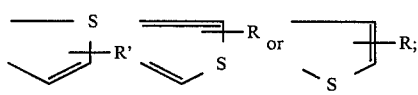

R is mono- or dihalo, amino, nitro, cyano, hydroxy, trifluoromethyl, mercapto, lower alkyl, lower alkoxy, alkanoyl, lowercycloalkyl, carboxy, alkoxycarbonyl, mono- or dilower alkyl substituted amino, alkanoylamino, lower alkyl thio, loweralkyl-sulfonyl, sulfamoyl, lower alkyl substituted sulfamoyl, phenyl or phenyl substituted with halo, lower alkyl, lower alkoxy, trifluoromethyl, hydroxy, amino, cyano or nitro; X and Y are each, independently, hydrogen or

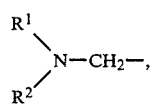

wherein $R^1$ is hydrogen or lower alkyl; $R^2$ is hydrogen or lower alkyl; or $R^1$ and $R^2$ taken together form a heterocyclic moiety selected from 1-pyrrolidinyl, 1-piperidinyl, 1-hexahydroazepinyl, 1-octahydroazocinyl, 3-thiazolidinyl, 4-morpholinyl or 4-thiomorpholinyl, with the proviso that one of X and Y is always hydrogen; n is 1–4; and the pharmacologically acceptable salts thereof.

The term "halo" refers to fluoro, chloro and bromo. The terms "lower alkyl" and "lower alkoxy" refer to moieties having 1–6 carbon atoms in the carbon chain. The term "lower cycloalkyl" refers to cyclic structures having 5 to 7 carbon atoms. The term "alkanoyl" refers to the moiety RCO— wherein R in an alkyl group having 1–4 carbon atoms.

The compounds of the invention can be readily prepared by reacting an appropriate 4-sulfamoyl-thiophene-3-carboxylate with an appropriate 3-substituted phenoxy-alkyl-propanamine according to the following sequence:

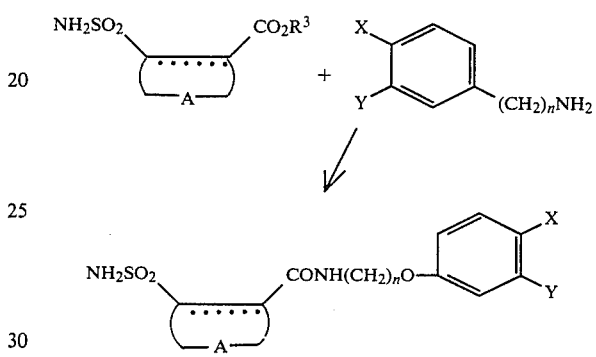

where A, X, Y and n are as hereinbefore defined and $R^3$ is hydrogen or lower alkyl.

The starting compound 4-sulfamoyl-3-carboxylic acid and its preparation are disclosed in U.S. Pat. No. 4,028,373. The starting alkylamine and its preparation are disclosed in U.K. Pat. No. 1,604,675, granted Dec. 16, 1981, to Allen & Hanburys Ltd.

The compounds of the invention readily form pharmacologically acceptable salts with both inorganic and organic acids such as hydrochloric, hydrobromic, sulfuric, nitric, phosphoric, acetic maleic, fumaric, citric, methanesulfonic, toluenesulfonic and the like.

The compounds of the invention are intermediates in the preparation of compounds having the formula:

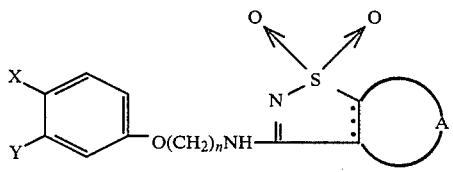

wherein A is a moiety having the formula:

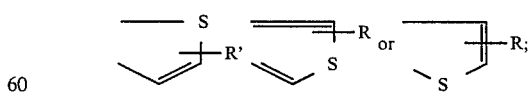

R in mono- or dihalo, amino, nitro, cyano, hydroxy, trifluoromethyl, mercapto, lower alkyl, lower alkoxy, alkanoyl, lowercycloalkyl, carboxy, alkoxycarbonyl, mono- or dilower alkyl substituted amino, alkanoylamino, lower alkyl thio, loweralkyl-sulfonyl, sulfamoyl, lower alkyl substituted sulfamoyl, phenyl or phenyl substituted with halo, lower alkyl, lower alkoxy, trifluoromethyl, hydroxy, amino, cyano or nitro; X and Y are each, independently, hydrogen or

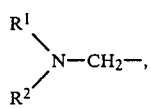

wherein R¹ is mono- or diloweralkylamino, mono- or di-N-loweralkylaminolower alkyl, (2-furyl)methylamino, benzylamino, lower cycloalkylamino, 1-pyrrolidinyl, 1-piperidinyl, 1-hexahydroazepinyl, 1-octahydroazocinyl, 3-thiazolidinyl, 4-morpholinyl or 4-thiomorpholinyl, with the proviso that one of X and Y is always hydrogen; n is 1 to 4, and the pharmacologically acceptable salts thereof, which compounds are disclosed and claimed in pending U.S. Ser. No. 468,221, now U.S. Pat. No. 4,490,527.

These compounds can be prepared from the intermediates of the present invention according to the following reaction sequence:

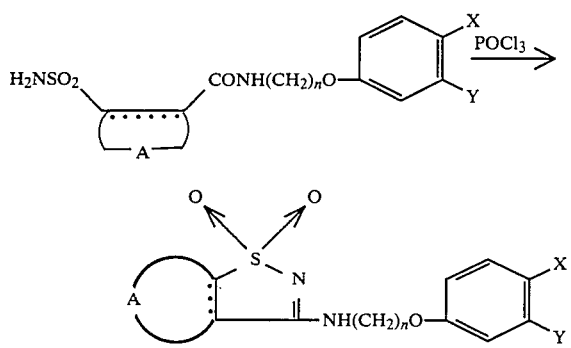

The reaction is carried out under reflux conditions and after recrystallization, gives a good yield of the desired final products.

The compounds of the invention have potent antisecretory/anti-ulcer activity and can be used in the treatment of conditions where there is hypersecretion of gastric acid, such as in gastric and peptic ulceration and other conditions caused or exacerbated by gastric activity such as stress ulceration or gastric intestinal bleeding due to trauma.

The compounds of the invention can be administered orally or parenterally or by suppository, of which the preferred route is the oral route. They may be used in the form of the base or as a pharmacologically acceptable salt. They will in general be associated with a pharmaceutically acceptable carrier or diluent, to provide a pharmaceutical composition.

The compounds of the invention can be administered in combination with other active ingredients, e.g. conventional antihistamines if required. For oral administration and pharmaceutical composition can most conveniently be in the form of capsules or tablets, which may be slow release tablets. The composition may also take the form of a dragee or may be in syrup form.

A convenient daily dose by the oral route would be of the order of 100 mg to 1.2 g per day, in the form of dosage units containing from 20 to 200 mg per dosage unit. A convenient regimen in the case of a slow release tablet would be twice or three times a day.

Parenteral administration may be by injections at intervals or as a continuous infusion. Injection solutions may contain from 10 to 100 mg/ml of active ingredient.

The antisecretory activity of the compounds of the invention may be demonstrated in the modified Shay procedure of pylorus ligation for the study of rat gastric secretion. The procedure for this test is presented at the end of the following example, which will serve to illustrate the present invention.

EXAMPLE 1

4-(Aminosulfonyl)N-[3-[3-(1-Piperidinylmethyl)-Phenoxy]Propyl]-3-Thiophenecarboxamide, Hydrochloride A stirred mixture of 2.2 g (0.01 mole) of methyl 4-sulfamoyl-thiophene-3-carboxylate (prepared according to the procedure described in U.S. Pat. No. 4,028,373) and 2.48 g (0.01 mole) of 3-3-(1-piperidinylmethyl)phenoxy-1-propanamine (prepared according to the procedure described in U.K. Pat. No. 1,604,675) is heated in an oil bath of 170° C. for 3 hours. The mixture is cooled to 100° C. and 15 ml of ethanol is added. The solution which forms is diluted with a small amount of water and is acidified to pH 1 with conc. hydrochloric acid. The precipitate which forms is collected and is recrystallized twice from ethanol to afford 0.2 g of product, m.p. 195°–7° C.

Analysis for: $C_{20}H_{28}ClN_3O_4S_2$, Calculated: C, 50.67; H, 5.95; N, 8.87, Found: C, 50.74; H, 6.02; N, 8.74.

EXAMPLE 2

The procedure for testing gastric secretion in the rat, a modification of the procedure of Shay et al., Gastroenterology, 26, 906–13 (1954) is carried out as follows:

Male Charles River rats weighing 200–300 grams are deprived of food but not water for 24 hours prior to use. Water is, however, withheld during the experiment. The rats are weighed, anesthetized, and the pylorus ligated according to the method of Shay et al. Treatment or vehicle control is then administered interduodenally (i.d.). Rats are housed 2/cage and sacrificed with $CO_2$ four hours after ligation. The stomachs are removed, rinsed, and contents emptied into a graduated centrifuge tube. The tubes are centrifuged for 20 minutes at 2,000 RPM and the volume of gastric juice recorded. Any samples obviously contaminated by feces, food or hemolysis are eliminated. An aliquot of each is frozen for later analysis of $Na^+$, $K^+$ and $Cl^-$ concentration. The pH is measured and 1 ml. of gastric juice is titrated with 0.1N NaOH to a pH of 7.0–7.4. Titratable acid output is calculated in microequivalents and the percent inhibition of acid output is calculated as follows:

$$\% \text{ Inhibition of Acid Output} = \frac{\text{Acid Output (control)} - \text{Acid Output (Drug)}}{\text{Acid Output (control)}} \times 100$$

When tested in this procedure, the compound of Example 1 showed at 63% inhibition of total acid output at a dose level of 8 mg/kg, evidencing significant antisecretory acitivity.

What is claimed is:

1. A compound having the formula:

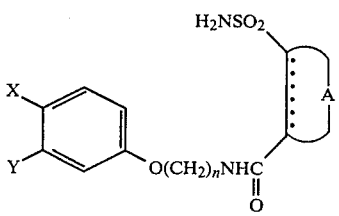

wherein
A is

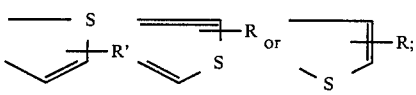

R is mono- or dihalo, amino, nitro, cyano, hydroxy, trifluoromethyl, mercapto, lower alkyl, lower alkoxy, alkanoyl of 2–5 carbon atoms, cycloalkyl of 5–7 carbon atoms, carboxy, alkoxycarbonyl of 2–7 carbon atoms, mono- or di-lower alkyl substituted amino, alkanoylamino of 2–5 carbon atoms, lower alkyl thio, loweralkyl-sulfonyl, sulfamoyl, lower alkyl substituted sulfamoyl, phenyl or phenyl substituted with halo, lower alkyl, lower alkoxy, trifluoromethyl, hydroxy, amino, cyano or nitro;

X and Y are each, independently, hydrogen or

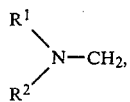

wherein $R^1$ is hydrogen or lower alkyl;

$R^2$ is hydrogen or lower alkyl; or $R^1$ and $R^2$ taken together form a heterocyclic moiety selected from 1-pyrrolidinyl, 1-piperidinyl, 1-hexahydroazepinyl, 1-octahydroazocinyl, 3, tetrahydrothiazolyl, 4-morpholinyl or 4-thiomorpholinyl, with the proviso that one of X and Y is always hydrogen;

n is 1–4;

and the pharmacologically acceptable salts thereof.

2. The compound of claim 1, which is 4-(aminosulfonyl)-N-[3-[3-(1-piperidinylmethyl)phenoxy]-propyl]-3-thiophenecarboxamide.

* * * * *